United States Patent [19]

Geke et al.

[11] Patent Number: 4,820,344

[45] Date of Patent: Apr. 11, 1989

[54] AQUEOUS COMPOSITIONS FOR VISUAL INSPECTION AND CLEANING OF METALLIC SURFACES

[75] Inventors: Juergen Geke; Bernhard Zange, both of Duesseldorf, Fed. Rep. of Germany

[73] Assignee: Henkel Kommanditgesellschaft auf Aktien, Duesseldorf, Fed. Rep. of Germany

[21] Appl. No.: 144,753

[22] Filed: Jan. 19, 1988

Related U.S. Application Data

[63] Continuation of Ser. No. 871,646, Jun. 6, 1986, abandoned.

[30] Foreign Application Priority Data

Jun. 20, 1985 [DE] Fed. Rep. of Germany ....... 3521952

[51] Int. Cl.$^4$ ................................................. C04B 9/02
[52] U.S. Cl. ..................... 106/14.13; 134/2; 134/41; 252/142
[58] Field of Search .................... 106/14.05, 14.13; 134/2, 41; 252/142

[56] References Cited

U.S. PATENT DOCUMENTS

| | | | |
|---|---|---|---|
| 2,822,358 | 2/1958 | Hearon et al. | 106/123.1 |
| 3,277,008 | 10/1966 | Hett | 252/142 |
| 3,717,433 | 2/1973 | Scherf et al. | |
| 3,897,349 | 7/1975 | Marin et al. | 252/33.3 |
| 4,073,618 | 2/1978 | Doi et al. | 252/855 E |
| 4,209,398 | 6/1980 | II et al. | 252/180 |
| 4,284,434 | 8/1981 | Lingmann et al. | 134/2 |
| 4,329,396 | 5/1982 | Kropp | 428/354 |
| 4,414,125 | 11/1983 | Keil et al. | 252/75 |
| 4,444,802 | 4/1984 | Winters et al. | 106/14.13 |
| 4,465,612 | 8/1984 | Altenschopfer et al. | 252/171 |

FOREIGN PATENT DOCUMENTS

| | | |
|---|---|---|
| 1084688 | 9/1980 | Canada . |
| 0020042 | 4/1980 | European Pat. Off. . |
| 2426114 | 2/1975 | Fed. Rep. of Germany . |
| 56-96081A | 8/1981 | Japan . |
| 56-96082A | 8/1981 | Japan . |
| 56-96083A | 8/1981 | Japan . |
| 57-32379A | 2/1982 | Japan . |
| 57-32380A | 2/1982 | Japan . |
| 57-32381A | 2/1982 | Japan . |
| 57-51267A | 3/1982 | Japan . |
| 57-51268A | 3/1982 | Japan . |
| 57-51272A | 3/1982 | Japan . |
| 57-108268 | 6/1982 | Japan . |
| 57-108269 | 6/1982 | Japan . |
| 57-108270 | 6/1982 | Japan . |
| 58-193377 | 11/1983 | Japan . |
| 58-193378 | 11/1983 | Japan . |
| 58-193379 | 11/1983 | Japan . |
| 59-219478 | 10/1984 | Japan . |
| 59-219479 | 10/1984 | Japan . |
| 59-219480 | 10/1984 | Japan . |
| 849110 | 9/1960 | United Kingdom . |
| 1042690 | 9/1966 | United Kingdom . |
| 2122598 | 6/1982 | United Kingdom . |

*Primary Examiner*—Theodore Morris
*Attorney, Agent, or Firm*—Ernest G. Szoke; Wayne C. Jaeschke; Mark A. Greenfield

[57] ABSTRACT

The invention relates to aqueous compositions containing one or more components selected from each of the groups comprising corrosion inhibitors, carboxylic acids, glycerol and derivatives, alcohols and polyethylene glycols, respectively, and tensides, which aqueous compositions are characterized in that they contain alkanolamines as the organic corrosion inhibitors, cinnamic acid and/or linear or branched aliphatic carboxylic acids or aromatic carboxylic acids as the carboxylic acids, glycerol and/or derivatives, dihydric alcohols and/or polyethylene glycols as the alcohols, cationic and/or nonionic tensides as the tensides and, optionally, UV-active ingredients, nonferrous metal inhibitors and/or light metal inhibitors and/or solubilizing agents. The compositions are used for preparing solutions suitable for the visual inspection and cleaning of surfaces of metallic structural members using the highlighting procedure or the flux procedure.

30 Claims, No Drawings

AQUEOUS COMPOSITIONS FOR VISUAL INSPECTION AND CLEANING OF METALLIC SURFACES

This application is a continuation of application Ser. No. 871,646, filed June 6, 1986, now abandoned.

BACKGROUND OF THE INVENTION

1. Field of the Invention

This invention relates to compositions to be used in metal treating, specifically visually inspecting and cleaning metallic surfaces using a highlighting procedure or flux procedure, particularly iron or steel automotive structural elements.

2. Statement of Related Art

Metal surfaces made of iron or steel, for example, metal surfaces suitable for use in the production of automotive bodies, are subjected to a visual inspection prior to the phosphation procedure. By such inspection, locations of surface damage or material unevenness are detected, and parts having undesired quality features may thus be rejected. This is important since surface unevenness will not only affect the quality of the anticorrosive phosphated layer, but also cause the occurence of irregularities in the subsequent protective layers, for example in the varnish or lacquer.

For the visual inspection of metallic surfaces in the automotive industry there have so far been used hydrocarbon mixtures (gasoline, kerosene, etc.) and aqueous formulations containing large amounts of organic solvents and nitrite salts. The aqueous compositions containing such components are applied directly to the metal surfaces, forming a continuous liquid film which allows irregularities on the metal surface to be readily recognized. In this manner, a visual check of the iron or steel surfaces is facilitated. This procedure is generally referred to as "highlighting."

There is an important drawback in the solvent formulations used in the highlighting procedure in that workers engaged in checking the metal surfaces are continuously exposed to the organic solvent vapors. In addition, it is sometimes necessary for the workers to touch the metal surfaces so that their skin is in contact with the formulations, which creates another health risk due to the solvent proportions and the nitrite content. Furthermore, such components require a thorough and expensive cleaning of the waste water before it can be disposed of, as neither organic solvents (such as hydrocarbons), nor nitrites are allowed to be discharged with waste water. Additionally, films obtained by using highlighting formulations based on water/organic solvent/nitrite show an insufficient film coherence on some metal surfaces which makes the visual inspection difficult.

The inspection of metallic surfaces by means of the "flux procedure" utilizes the fact that iron filings become oriented in a magnetic field. A liquid containing fine iron filings is sprayed or poured onto a metal surface. Fissures in the metal surface are indicated in that the iron filings are irregularly orientated above the fissure location. The flux procedure usually employs aqueous formulations. The flux process is described in further detail in German Industrial Standard (DIN) 54,132. A drawback in the procedure is that mostly films having only a low coherence are formed, which do not allow a successful inspection of the metallic surfaces to be performed. Also, such formulations have proven to promote corrosion markedly, so that the quality of the coatings obtained by the subsequent application of coating materials is significantly affected. Moreover, the visual surface inspection is only one of several stages of preparation for the actual coating process. In the above conventional procedures it happens time and again that materials are introduced which promote foaming or other undesired side-effects.

DESCRIPTION OF THE INVENTION

The present invention provides aqueous compositions for use in the highlighting or flux procedures which do not contain any hydrocarbons or chlorinated hydrocarbons or other ecologically objectionable organic solvents or nitrite. The present invention also provides dermatologically acceptable formulations usable for manual application in these procedures, as well as aqueous compositions which, when used in the highlighting or flux procedures, give a coherent, transparent, bubble-free, liquid film on the metal surface immediately after application. The present invention further provides formulations for use in the procedures, all components of which are compatible with UV-sensitizing active ingredients, whose presence is capable of further improving the range of application.

To achieve the above, this invention employs aqueous compositions containing: (A) organic corrosion inhibitors, (B) carboxylic acids, (C) glycerol and/or its derivatives, (D) polyalcohols and/or polyethylene glycols and (E) biodegradable tensides (surfactants). The formulations according to the invention may optionally contain: (F) UV-active compounds, (G) nonferrous metal inhibitors, (H) light metal inhibitors and/or (I) solubilizing agents, all in (J) a water base.

Thus the present invention includes both the above aqueous compositions as concentrates and in diluted form ready for use, as well as methods for their use in both highlighting procedures and flux procedures.

Other than in the operating examples, or where otherwise indicated, all numbers expressing quantities of ingredients, reaction conditions, or defining ingredient parameters used herein are to be understood as modified in all instances by the term "about." All percentages by weight of ingredients are based upon the total weight of the inventive composition concentrate, unless stated otherwise. Details of the individual ingredients are as follows.

(A) The corrosion inhibitors contained in the aqueous compositions according to the present invention comprise alkanolamine, preferably $C_{1-4}$ alkanol, most preferably monoethanolamine, diethanolamine or triethanolamine. The content of such organic corrosion inhibitors is 5 to 40% preferably 10 to 25% by weight.

(B) The carboxylic acids are at least one of:

(1) cinnamic acid (3-phenyl-2-propenoic acid);

(2) linear or branched aliphatic carboxylic acid having the general formula $$C_mH_{2m+1}COOH \qquad (I)$$

wherein m is an integer from 5 to 17, preferably 8 to 12; or (3) aromatic carboxylic acid having the general formula

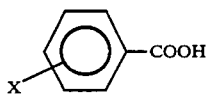

(II)

wherein x is —H, —NO$_2$, —COOH, —OH, —SO$_3$H, or a linear or branched alkyl of the formula C$_n$H$_{2n+1}$ where n is an integer from 1 to 4.

More specifically, as the aliphatic carboxylic acids there may be used, for example, caproic acid, caprylic acid, capric acid, lauric acid, myristic acid, palmitic acid, stearic acid, isohexanoic acid, 2-ethylhexanoic acid or isononanoic acid. Caprylic, capric, lauric, and/or isononanoic acids are particularly preferred. However, other straight-chain or branched aliphatic carboxylic acids are also suitable for the aqueous compositions according to the present invention. As the aromatic carboxylic acids there may be specifically mentioned benzoic acid, nitrobenzoic acid, phthalic acid, isophthalic acid, terephthalic acid, salicylic acid, p-hydroxybenzoic acid, o-toluylic acid or p-toluylic acid. Benzoic acid is particularly preferred.

The at least one carboxylic acid content of the concentrate is 5 to 25%, preferably 5 to 15%, most preferably 10 to 15%, by weight.

(C) The glycerol and/or a derivative thereof is preferably at least one glycerol or polyglycerol, and is present in the concentrate in 3 to 50%, preferably 10 to 40%, most preferably 10 to 30%, by weight.

(D) The polyalcohol and/or polyethylene glycol is preferably at least one dihydric alcohol, alcohol ether, or polyethylene glycol. Preferred alcohols are diethylene glycol, propylene glycol and/or 2-methyl-2,4-pentane diol. In addition to or in the place of the dihydric alcohols there may also be used alcohol ethers such as alkoxylated alkylene glycols, for example ethoxylated ethylene glycol. The number average molecular weights of such alcohol ethers are in the range between 300 to 1,000.

As alcohol components for the aqueous compositions polyethylene glycols are also usable with advantage. The number average molecular weight of these compounds are within the range 200 to 1,000.

The at least one polyalcohol and/or polyethylene glycol content of the concentrate is 10 to 70%, preferably 15 to 60%, most preferably 25 to 60%.

(E) The biodegradable tenside is at least one sprayable and low-foaming cationic and/or nonionic tenside (surfactant) or mixture of tensides.

Preferred as the usable nonionic tensides are alcohols or alkylphenols which have been ethoxylated or propoxylated, respectively, by reaction with ethylene oxide and/or propylene oxide. However, there may also advantageously be used polyethylene glycoethers having the formula R$^1$O—(CH$_2$CH$_2$O)$_p$—R$^2$ (III)

wherein:
R$^1$ is a straight or branched alkyl or alkenyl residue having from 8 to 18 carbon atoms;
R$^2$ is an alkyl residue having from 4 to 8 carbon atoms; and
p is an integer of from 7 to 12.

There may also be used polyethylene glycolethers obtainable by the addition of from 4 to 20 parts by weight of ethylene oxide to 1 part by weight of polyglycerol having a hydroxyl value of from 900 to 1,200 with subsequent etherification of the free hydroxyl moieties with straight-chain or branched C$_{4-8}$-alkyl halides. The two latter groups of nonionic tensides are generally denominated as "end-capped mixed ether tensides."

Preferred for use as the cationic tenside are ammonium compounds wherein at least two substituents at the nitrogen atom are C$_{1-3}$ alkyl moieties, preferably methyl moieties, and at least one further substituent is an optionally substituted C$_{8-12}$ alkyl moiety. The anions of the cationic tensides usually are those which impart good water-solubility to the cationic tensides. Preferred for use as cationic tensides are lauryldimethylbenzylammonium chloride and/or benzyldimethyl-2-hydroxydodecylammonium isononanoate.

The at least one biodegradable tenside content of the concentrate is 2 to 10%, preferably 2 to 7%, most preferably 5 to 7%, by weight.

(F) The at least one UV (ultraviolet)-active compound is preferably fluorescein, although any compatible UV-sensitive water-soluble substance may be used.

The at least one UV-active ingredient may be present in the concentrate in 0 to 0.5% and when used, in from a minimally UV-detectable amount up to 0.5%, most preferably up to 0.005%, by weight.

(G) The nonferrous metal inhibitor is at least one of tolyl triazole or benzotriazole.

The at least one nonferrous metal inhibitor may be present in the concentrate in 0 to 0.5%, and when used, preferably in from a minimally nonferrous metal inhibitive amount to up to 0.5%, most preferably in 0.1 to 0.5%, by weight.

(H) The light metal inhibitor is at least one sodium alkylether phosphate.

The at least one light metal inhibitor may be present in the concentrate in 0 to 5.0%, when used, preferably in from a minimally light metal inhibitive effective amount to up to 5.0%, most preferably in 0.5 to 5.0% by weight.

(I) The solubilizing agent is at least one sulfonate, preferably cumol sulfonate and/or lignin sulfonate.

The at least one solubilizing agent may be present in the concentrate in 0 to 10%, when used, preferably in from a minimally solubilizing effective amount up to 10%, more preferably in 0.1 to 10.0%, most preferably in 4 to 6%, by weight.

(J) Water is the base for the concentrate solution, and must be present in a quantity sufficient (q.s.) to make up 100%. Generally, especially when at least one optional ingredient is present, the amount of water in the concentrate will be 5 to 20%, preferably 9 to 16%, by weight. No particular purity of water is required, although it should not contain substantial amounts of interfacing ions or solids.

The aqueous compositions according to the present invention are marketed as concentrates having the compositions as set forth hereinabove. However, in practice, application is hardly ever in the concentrate form. The concentrate are rather diluted with water so that aqueous solutions of from 2 to 20% of the total aqueous concentrates are formed.

Such solutions may be used at any concentration range for the visual inspection of metallic surfaces, using the highlight procedure or flux procedure.

The aqueous compositions according to the invention may be applied in concentrated or diluted form onto the metal surfaces by splashing, by spraying or by manual application. By means of said solutions a thorough and accurate visual inspection of the metal surfaces is possible with the mentioned procedures. In all cases a coherent liquid film is formed. Thereby, the metal surfaces are not only rid of residual contaminations, but they are also protected from corrosion, while no foam-forming or otherwise interfering liquid residues will be introduced into the subsequent process steps. Even when spraying devices are employed, the use of the solutions at room temperature is possible, without any interfering foam being formed. Furthermore, the use of the aqueous compositions according to the invention does not result in any health hazards or ecological risks. Thus, the inventive compositions have additional aspects of cleaning the metal surfaces being examined and protecting them from corrosion.

The present invention is further illustrated by the following non-limiting examples.

a. Preparation of the compositions according to the present invention

The components as set forth in the individual examples were successively added to the amount of water, tap water having been used in all cases.

b. Test method

1. Preparation of sheets:

Steel sheets of grade St 1405 (15 cm×30 cm) were cleaned manually or in a laboratory splash device using a 1.5% or 2% solution of a neutral cleaner at from 50° C. to 60° C. and were dried using cold air or hot air as the alternatives.

2. Product application:

The product concentration according to the present invention was diluted with water and then applied onto on above sheet which had thus been cleaned and cooled.

The following modes of application were chosen:

Manual spraying using a hand spray bottle; concentration of the aqueous concentrate compositions: 5 to 10% by weight; or Manual application using a soft cloth rag or sponge; concentration of the aqueous concentrate compositions: 10 to 15% by weight; or Splashing; concentration of the aqueous concentrate compositions: 2 to 4% by weight.

3. Assessment of the surfaces:

The compositions according to the invention ensured that the metal surfaces were uniformly wetted. The formed product films were completely coherent for a period of at least 6 minutes. During this period, the metal surfaces remained wet and glossy so that a visual inspection of the surface quality could be readily performed.

4. Protection from corrosion:

The product films formed by the aqueous compositions according to the present invention temporarily protected the treated metal surfaces from corrosion. The protection from corrosion was effective on the treated steel plates in a laboratory atmosphere for at least two weeks.

5. Removability:

The films formed on the metal surfaces by the aqueous compositions according to the present invention were readily removable by use of respective cleaners of a degreasing or phosphating line or by use of neutral cleaners such as, e.g., those employed in accordance with the flux procedure.

c. Components of the aqueous concentrate compositions and amounts thereof in weight %

EXAMPLE 1

| % | (Suitable for manual or spray application) Ingredient |
|---|---|
| 10.0 | cinnamic acid |
| 10.0 | diethanolamine; |
| 35.0 | an ethoxylated ethylene glycol, number average molecular weight of 400; |
| 7.0 | polyglycerol; |
| 15.0 | 2-methyl-2,4-pentane diol; |
| 0.2 | tolyl triazole; |
| 2.0 | sodium alkylether phosphate[1]; |
| 2.5 | a modified polyethoxylated straight chain alcohol, a nonionic tenside with an HLB of 11.6[2]; |
| 2.5 | an addition product of 3 mols ethylene oxide and 6 mols propylene oxide to a $C_{12-18}$ alcohol; and |
| 15.8 | water. |
| 100.0 | |

Notes:
[1]"Forlanit" P, a trademark of Henkel KGaA, Dusseldorf, Germany
[2]"Triton" DF 16, a trademark of Rohm & Haas, Co., Philadelphia, Pennsylvania, U.S.A.

EXAMPLE 2

| % | (Suitable for manual, spray and splash application at and above room temperature) Ingredient |
|---|---|
| 15.0 | diethanolamine; |
| 10.0 | isononaoic acid; |
| 30.0 | glycerol; |
| 20.0 | 2-methyl-2,4-pentane diol; |
| 5.0 | tetraethylene glycol; |
| 4.0 | an addition product of 3 mols ethylene oxide and 6 mols propylene oxide to a $C_{12-18}$ alcohol; |
| 1.0 | benzyllauryldimethylammonium chloride; |
| 0.0025 | fluorescein; and |
| 14.9975 | water. |
| 100.0 | |

EXAMPLE 3

| % | (Suitable for manual, spray and splash application) Ingredient |
|---|---|
| 3.0 | monoethanolamine; |
| 20.0 | triethanolamine; |
| 5.0 | isononaoic acid; |
| 3.0 | caprylic acid; |
| 5.0 | 2-ethylhexanoic acid; |
| 25.0 | 2-methyl-2,4-pentane diol; |
| 10.0 | an ethoxylated ethylene glycol, number average molecular weight of 400; |
| 12.0 | glycerol; |
| 4.0 | an addition product of 3 mols ethylene oxide and 6 mols propylene oxide to a $C_{12-18}$ alcohol; and |
| 1.0 | benzyllauryldimethylammonium chloride; and |
| 12.0 | water. |
| 100.0 | |

EXAMPLE 4

| % | (Suitable for manual, spray and splash application at and above room temperature) Ingredient |
|---|---|
| 15.0 | diethanolamine; |
| 7.0 | isononaoic acid; |
| 3.0 | benzoic acid; |
| 16.0 | glycerol; |
| 4.0 | diethylene glycol; |
| 23.0 | 2-methyl-2,4-pentane diol; |

-continued

| % | Ingredient |
|---|---|
| | (Suitable for manual, spray and splash application at and above room temperature) |
| 13.0 | an ethoxylated ethylene glycol, number average molecular weight of 400; |
| 4.0 | an addition product of 3 mols of ethylene oxide and 6 mols of propylene oxide to a $C_{12-18}$ alcohol; |
| 1.0 | benzyllauryldimethylammonium chloride; |
| 5.0 | lignin sulfonate; and |
| 9.0 | water. |
| 100.0 | |

We claim:

1. An aqueous concentrate composition for use in visually inspecting metal surfaces using a highlighting procedure or flux procedure consisting essentially of:
   (A) an organic corrosion inhibitor which is at least one $C_{1-4}$ alkanolamine, present in about 5 to 40% by weight;
   (B) at least one carboxylic acid selected from
      (1) cinnamic acid;
      (2) a linear or branched aliphatic carboxylic acid having the general formula

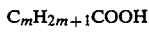

$$C_mH_{2m+1}COOH$$

wherein m is an integer from 5 to 17; or
      (3) aromatic carboxylic acid having the general formula

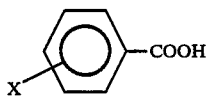

(II)

wherein x is —H, —NO$_2$, —COOH, —OH, —SO$_3$H, or a linear or branched alkyl of the formula $C_nH_{2n+1}$ where n is an integer from 1 to 4, present in about 5 to 25% by weight;
   (C) at least one glycerol and/or polyglycerol, present in about 3% to 50% by weight;
   (D) at least one dihydric alcohol, alcohol ether or polyethylene glycol present in about 10 to 70% by weight;
   (E) at least one biodegradable cationic or nonionic tenside present in about 2 to 10% by weight;
   (F) at least one ultraviolet-active compound, present in 0 to up to about 0.5% by weight;
   (G) at least one nonferrous metal inhibitor, present in 0 to up to about 0.5% by weight;
   (H) at least one light metal inhibitor, present in 0 to up to about 5.0% by weight:
   (I) at least one solubilizing agent, present in 0 to about 10% by weight; and
   (J) water, q.s. to 100% of concentrate.
2. The concentrate of claim 1 wherein:
   (A) is monoethanolamine, diethanolamine, triethanolamine, or any mixture thereof.
3. The concentrate of claim 1 wherein:
   (B) is cinnamic acid.
4. The concentrate of claim 1 wherein:
   (B) is said aliphatic carboxylic acid and has 8 to 12 carbon atoms.
5. The concentrate of claim 1 wherein:
   (B) is at least one of caproic, caprylic, capric, lauric, myristic, plamitic, stearic, isohexanoic, 2-ethylhexanoic, or isononanoic acids.
6. The concentrate of claim 1 wherein:
   (B) is at least one of caprylic, capric, lauric, or isononanoic acids.
7. The concentrate of claim 1 wherein:
   (B) is at least one of benzoic, nitrobenzoic, phthalic, isophthalic, terephthalic, salicylic, p-hydroxybenzoic, o-toluylic or p-toluylic acids.
8. The concentrate of claim 1 wherein:
   (B) is benzoic acid.
9. The concentrate of claim 1 wherein:
   (C) is at least one glycerol or polyglycerol.
10. The concentrate of claim 1 wherein:
    (D) is at least one dihydric alcohol, alkoxylated alkylene glycol, or polyethylene glycol.
11. The concentrate of claim 1 wherein:
    (D) is at least one of diethylene glycol, propylene glycol, 2-methyl-2,4-pentane diol, ethoxylated ethylene glycol having a number average molecular weight between 300 and 1,000, or polyethylene glycol having a number average molecular weight between 200 and 1,000.
12. The concentrate of claim 1 wherein:
    (E) is at least one cationic tenside which is an ammonium compound wherein at least two substituents at the nitrogen atom are $C_{1-3}$-alkyl moieties and at least one further substituent is a substituted or unsubstituted $C_{8-12}$-alkyl moiety; or at least one nonionic tenside which is: an alcohol or alkylphenol which has been ethoxylated or propoxylated; a polyethylene glycol ether of the formula $R^1O$—$(CH_2CH_2O)_p$—$R^2$, wherein $R^1$ is a straight or branched $C_{8-18}$-alkyl or $C_{8-18}$-alkenyl residue, $R^2$ is a $C_{4-8}$-alkyl residue, and p is an integer from 7 to 12; or a polyethylene glycol ether obtained by the addition of 4 to 20 parts by weight of ethylene oxide to 1 part by weight of polyglycerol having a hydroxyl value of from 900 to 1,200 with subsequent etherification of the free hydroxyl moieties with straight chain or branched $C_{4-8}$-alkyl halides.
13. The concentrate of claim 12 wherein said at least one cationic tenside is lauryldimethylbenzylammonium chloride or benzyldimethyl-2-hydroxydodecylammonium isononanoate.
14. The concentrate of claim 1 wherein:
    (F) is present and is fluorescein.
15. The concentrate of claim 1 wherein:
    (G) is present and is tolyl triazole, benzotriazole, or any mixture thereof.
16. The concentrate of claim 1 wherein:
    (H) is present and is at least one sodium alkylether phosphate.
17. The concentrate of claim 1 wherein:
    (I) is present and is at least one sulfonate.
18. The concentrate of claim 1 wherein:
    (I) is present and is cumol sulfonate, lignin sulfonate, or any mixture thereof.
19. The concentrate of claim 1 wherein:
    (A) is monoethanolamine, diethanolamine, triethanolamine, or any mixture thereof
    (B) is at least one of:
       (1) cinnamic acid,
       (2) caproic, caprylic, capric, lauric, myristic, palmitic, stearic, isohexanoic, 2-ethylhexanoic, or isononanoic acids, (3) benzoic, nitrobenzoic, phthalic, isophthalic, terephthalic, salicylic, p-hydroxybenzoic, o-toluylic or p-toluylic acids, (C) is at least one glycerol or polyglycerol;

(D) is at least one of diethylene glycol, propylene glycol, 2-methyl-2,4-pentane diol, ethoxylate ethylene glycol having a number average molecular weight between 300 and 1,000, or polyethylene glycol having a number average molecular weight between 200 and 1,000; and (E) is at least one cationic tenside which is an ammonium compound wherein at least two substituents at the nitrogen atom are $C_{1-3}$-alkyl moieties and at least one further substituent is a substituted or unsubstituted $C_{8-12}$-alkyl moiety; or at least one non-ionic tenside which is: an alcohol or alkylphenol which has been ethoxylated or propoxylated; a polyethylene glycol ether of the formula $R^1O-(CH_2CH_2O)_p-R^2$, wherein $R^1$ is a straight or branched $C_{8-18}$-alkyl or $C_{8-18}$-alkenyl residue, $R^2$ is a $C_{4-8}$-alkyl residue, and p is an integer from 7 to 12; or a polyethylene glycol ether obtained by the addition of 4 to 20 parts by weight of ethylene oxide to 1 part by weight of polyglycerol having a hydroxyl value of from 900 to 1,200 with subsequent etherification of the free hydroxyl moieties with straight chain or branched $C_{4-8}$-alkyl halides.

20. The concentrate of claim 19 wherein:
(F) is present and is fluorescein.

21. The concentrate of claim 19 wherein:
(G) is present and is tolyl triazole, benzotriazole, or any mixture thereof.

22. The concentrate of claim 19 wherein:
(H) is present and is at least one sodium alkylether phosphate.

23. The concentrate of claim 19 wherein:
(I) is present and is at least one sulfonate.

24. The concentrate of claim 19 wherein:
(I) is present and is cumol sulfonate, lignin sulfonate, or any mixture thereof.

25. The concentrate of claim 1 wherein:
(A) is present in about 10 to 25% by weight;
(B) is present in about 5 to 15% by weight;
(C) is present in about 10 to 40% by weight;
(D) is present in about 15 to 60% by weight; and
(E) is present in about 2 to 7% by weight.

26. The concentrate of claim 19 wherein:
(A) is present in about 10 to 25% by weight;
(B) is present in about 5 to 15% by weight;
(C) is present in about 10 to 40% by weight;
(D) is present in about 15 to 60% by weight; and
(E) is present in about 2 to 7% by weight.

27. The concentrate of claim 1 wherein:
(A) is present in about 10 to 25% by weight;
(B) is present in about 10 to 15% by weight;
(C) is present in about 10 to 30% by weight;
(D) is present in about 25 to 60% by weight; and
(E) is present in about 5 to 7% by weight.

28. The concentrate of claim 19 wherein:
(A) is present in about 10 to 25% by weight;
(B) is present in about 10 to 15% by weight;
(C) is present in about 10 to 30% by weight;
(D) is present in about 25 to 60% by weight; and
(E) is present in about 5 to 7% by weight.

29. A metal treating solution comprising about 2 to 20% by weight of the concentrate of claim 1 diluted with water q.s. to 100%.

30. A metal treating solution comprising about 2 to 20% by weight of the concentrate of claim 19 diluted with water q.s to 100%.

* * * * *